United States Patent

Esser et al.

[11] Patent Number: 5,712,397
[45] Date of Patent: Jan. 27, 1998

[54] AMINO ACID DERIVATIVES, PROCESSES FOR PREPARING THEM AND PHARMACEUTICAL COMPOSITIONS CONTAINING THESE COMPOUNDS

[75] Inventors: Franz Esser, Ingelheim am Rhein; Gerd Schnorrenberg, Gau-Algesheim; Horst Dollinger, Ingelheim am Rhein; Birgit Jung, Bingen am Rhein; Erich Burger, Bingen am Rhein; Georg Speck, Ingelheim am Rhein, all of Germany

[73] Assignee: Boehringer Ingelheim GmbH, Ingelheim am Rhein, Germany

[21] Appl. No.: 467,428

[22] Filed: Jun. 6, 1995

Related U.S. Application Data

[63] Continuation of Ser. No. 398,257, Mar. 3, 1995.

[30] Foreign Application Priority Data

Mar. 3, 1994 [DE] Germany .................. 44 06 884.0

[51] Int. Cl.⁶ .................. C07D 491/56; C07D 221/06; C07D 215/227
[52] U.S. Cl. .................. 546/90; 546/110; 546/158
[58] Field of Search .................. 546/83, 84, 90, 546/101, 110, 158; 514/293, 290, 312

[56] References Cited

U.S. PATENT DOCUMENTS

| | | | |
|---|---|---|---|
| 4,692,522 | 9/1987 | Parsons | 540/523 |
| 5,162,339 | 11/1992 | Lowe, III | 514/305 |
| 5,472,978 | 12/1995 | Baker | 524/443 |

FOREIGN PATENT DOCUMENTS

| | | |
|---|---|---|
| 0166357 | 1/1986 | European Pat. Off. . |
| 9216524 | 10/1992 | WIPO . |
| 9405693 | 3/1994 | WIPO . |

OTHER PUBLICATIONS

"A Nonpeptidyl Growth Hormone Secretagogue"—*Science*—vol. 260, Jun. 11, 1993, pp. 1640–1643.

Vaught, JL (1988) Life Sci. 43, 1419–31.

*Primary Examiner*—C. Warren Ivy
*Assistant Examiner*—Evelyn Huang
*Attorney, Agent, or Firm*—R. P. Raymond; M-E. M. Devlin; A. R. Stempel

[57] ABSTRACT

The invention relates to new amino acid derivatives of general formula I

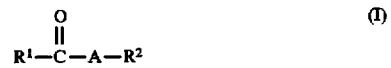

and the pharmaceutically acceptable salts thereof, wherein the group $R^2$ is

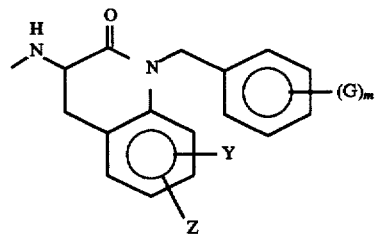

and $R^1$, A, G, Y, Z and m have the meanings given in the specification, and the preparation and use thereof. The new compounds are valuable neurokinin (tachykinin)-antagonists.

2 Claims, No Drawings

AMINO ACID DERIVATIVES, PROCESSES FOR PREPARING THEM AND PHARMACEUTICAL COMPOSITIONS CONTAINING THESE COMPOUNDS

This is a continuation, of application Ser. No. 08/398, 257, filed Mar. 3, 1995.

The invention relates to new amino acid derivatives of general formula I

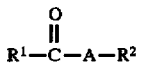

and the pharmaceutically acceptable salts thereof, processes for preparing them and pharmaceutical compositions containing these compounds. The compounds are useful neurokinin (tachykinin)-antagonists.

European Patent Applications EP 394 989 and EP 443 132 describe peptides with a neurokinin-antagonistic activity.

German Patent Application P 43 15 437.9 describes compounds which differ from these peptides essentially in the $R^2$ component. The new compounds of the present invention are selected from the compounds generally defined in P 43 15 437.9.

The abbreviations used for the amino acids in this specification and in the claims correspond to the conventional three-letter code as described, for example, in Europ. J. Biochem., 138, 9 (1984). The other abbreviations are explained as follows:

| |
|---|
| Boc = t-Butoxycarbonyl |
| Bzl = Benzyl |
| CDI = Carbonyldiimidazole |
| DCCI = Dicyclohexylcarbodiimide |
| DCH = Dicyclohexylurea |
| HOBt = 1-Hydroxybenzotriazole |
| Hyp = (2S,4R)-Hydroxyproline |
| THF = Tetrahydrofuran |
| TEA = Triethylamine |
| TFA = Trifluoroacetic acid |
| Z = Benzyloxycarbonyl |
| Me = Methyl |
| Ac = Acetyl |
| Et = Ethyl |
| DMF = Dimethylformamide |
| DPPA = Diphenylphosphoryl azide |
| PPA = Polyphosphoric acid |
| RT = Room temperature |
| TBTU = Benzotriazolyl-tetramethyl-uronium tetrafluoroborate |

Unless specifically stated otherwise in the text which follows, the term amino acid includes natural and unnatural amino acids, both the D-form and the L-form, particularly α-amino acids, and the isomers thereof.

If an amino acid is given without a prefix (e.g. Orn) this refers to the L-form of the amino acid. The D-form is specifically stated.

The invention relates to new amino acid derivatives of the general formula I

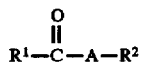

or the pharmaceutically acceptable salts thereof, wherein
$R^1$ denotes vinyl, aryl, heteroaryl, aralkyl, heteroaralkyl, arylvinyl, heteroarylvinyl, aryloxyalkyl, arylalkyloxy, $(C_3-C_8)$cycloalkyl, $(C_3-C_8)$cycloalkylalkyl, unsubstituted or mono-, di- or tri-methyl-substituted bicycloheptyl or bicycloheptylalkyl, adamantyl, adamantylalkyl, decalin, decalinalkyl, tetralin, tetralinalkyl, diphenylalkyl, di(arylalkyl)aminoalkyl or arylalkylaminoalkyl (wherein aryl denotes phenyl, mono-, di- or tri-substituted phenyl or naphthyl; the substituents of the phenyl group independently of one another denote halogen, trihalomethyl, alkoxy, alkyl, hydroxy, nitro, alkylcarbonyl or cyano; heteroaryl denotes indolyl, indolyl substituted in position 1 by alkyl or benzyl, pyridyl, pyrrolyl, imidazolyl or thienyl; and the alkyl or alkoxy group contains 1 to 3 carbon atoms);

A denotes D- or L-alanine (Ala), (D- or L-valine (Val), D- or L-leucine (Leu), D- or L-isoleucine (Ile), D- or L-serine (Ser), D- or L-threonine (Thr), D- or L-allothreonine, D- or L-cysteine (Cys), D- or L-methionine (Met), D- or L-phenylalanine (Phe), D- or L-tryptophan (Trp), N-formyl protected Trp, D- or L-tyrosine (Tyr), D- or L-proline (Pro), D- or L-didehydroproline (ΔPro) such as for example 3,4-didehydroproline (Δ(3,4)-Pro), D- or L-hydroxyproline (Pro(OH)) such as for example 3-hydroxyproline (Pro (3OH)) and 4-hydroxyproline (Pro(4OH)), D- or L-azetidine-2-carboxylic acid (Azt), D- or L-thioproline (Tpr), D- or L-aminoproline (Pro(NH₂)) such as, for example, 3-aminoproline (Pro(3NH₂)) and 4-aminoproline (Pro (4NH₂)), D- or L-pyroglutaminic acid (pGlu), D- or L-2-aminoisobutyric acid (Aib), D- or L-2,3-diaminopropionic acid, D- or L-2,4-diaminobutyric acid, D- or L-glutaminic acid (Glu), D- or L-aspartic acid (Asp), D- or L-glutamine (Gln), D- or L-asparagine (Ash), D- or L-lysine (Lys), D- or L-arginine (Arg), D- or L-histidine (HIS), D- or L-ornithine (Orn), D- or L-hydroxypiperidinocarboxylic acid such as, for example, 5-hydroxypiperidine-2-carboxylic acid, D- or L-mercaptoproline (Pro(SH)) such as, for example, 3-mercaptoproline (Pro(3SH)) and 4-mercaptoproline (Pro(4SH)), Tpr(O), Met(O), Tpr(O₂) or Met(O₂), and the geometric isomers thereof, whilst any hydroxy and amino groups which they may contain may be protected by conventional protecting group (e.g. acyl, carbamoyl or aralkyl (particularly benzyl);

$R^2$ denotes an amine of formula II

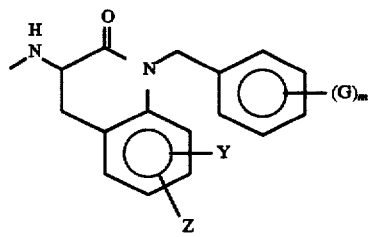

wherein
G is fluorine, chlorine, bromine, methyl, ethyl or methoxy
m denotes 1, 2, 3, 4 or 5;
Y and Z independently of each other represent hydrogen, $(C_{1-5})$alkyl, $(C_{1-5})$alkyloxy, benzyloxy [wherein the phenyl group is unsubstituted or has 1, 2 or 3 substituents which, independently of each other, are $(C_{1-5})$alkyl, preferably methyl, $(C_{1-5})$ alkoxy, preferably methoxy, dimethylamine, halogen, trifluoromethyl, —CN or —OCF₃], —OCF₃, halogen, —CF₃, —CN, —CH₂NH₂, —CONH₂, —N—(C₁₋₅-alkyl)₂, —NH—(C₁₋₄)-alkylcarbonyl, —N—(C₁₋₅)-alkyl—N—(C₁₋₄)-alkylcarbonyl, —NH₂ or NH—(C₁₋₅)-alkyl or, if Y and Z are arranged vicinally to each other, they together represent —OCH₂O—, —OCH₂CH₂O— or —(CH₂)₄—.

Compounds of general formula I may have acid groups, primarily carboxyl groups, or phenolic hydroxy groups, and/or basic groups such as guanidino or amino functions. Compounds of general formula I may therefore be obtained either as internal salts, as salts with pharmaceutically acceptable inorganic acids such as hydrochloric acid, sulphuric acid, phosphoric acid or sulphonic acid, or organic acids (such as, for example, maleic acid, fumaric acid, citric acid, tartaric acid or acetic acid) or as salts with pharmaceutically acceptable bases such as alkali or alkaline earth metal hydroxides or carbonates, zinc or ammonium hydroxides or organic amines such as diethylamine, triethylamine, triethanolamine, etc.

The chiral centres in the new amino acid derivatives may each have the R-, S- or R,S-configurations.

Of the compounds of formula I according to the invention, the preferred compounds are those wherein $R^1$ denotes vinyl, aryl, heteroaryl, aralkyl, heteroaralkyl, arylvinyl, heteroarylvinyl, aryloxyalkyl, arylalkyloxy, di(arylalkyl)aminoalkyl or arylalkylaminoalkyl (wherein aryl denotes phenyl, mono-, di- or tri-substituted phenyl or naphthyl; the substituents of the phenyl group independently of one another are halogen, trihalomethyl, alkoxy, alkyl or cyano; heteroaryl denotes indolyl, indolyl substituted in the 1-position by alkyl or benzyl, pyridyl, pyrrolyl, imidazolyl or thienyl; and the alkyl or alkoxy group contains 1 to 3 carbon atoms);

A denotes D- or L-alanine (Ala), D- or L-valine (Val), D- or L-leucine (Leu), D- or L-isoleucine (Ile), D- or L-serine (Ser), D- or L-threonine (Thr), D- or L-allothreonine, D- or L-cysteine (Cys), D- or L-methionine (Met), D- or L-phenylalanine (Phe), D- or L-tryptophan (Trp), N-formyl-protected Trp, D- or L-tyrosine (Tyr), D- or L-proline (Pro), D- or L-didehydroproline (ΔPro) such as, for example, 3,4-didehydroproline (Δ (3,4)-Pro), D- or L-hydroxyproline (Pro(OH)) such as, for example, 3-hydroxyproline (Pro(3OH)) and 4-hydroxyproline (Pro (4OH)), D- or L-azetidine-2-carboxylic acid (Azt), D- or L-thioproline (Tpr), D- or L-aminoproline (Pro (NH$_2$)) such as, for example, 3-aminoproline (Pro (3NH$_2$)) and 4-aminoproline (Pro (4NH$_2$)), D- or L-pyroglutaminic acid (pGlu), D- or L-2-aminoisobutyric acid (Aib), D- or L-2,3-diaminopropionic acid, D- or L-2,4-diaminobutyric acid, D- or L-glutamic acid (Glu), D- or L-aspartic acid (Asp), D- or L-glutamine (Gln), D- or L-asparagine (Asn), D- or L-lysine (Lys), D- or L-arginine (Arg), D- or L-histidine (His), D- or L-ornithine (Orn), D- or L-hydroxypiperidinocarboxylic acid such as, for example, 5-hydroxypiperidine-2-carboxylic acid, D- or L-mercaptoproline (Pro(SH)) such as, for example, 3-mercaptoproline (Pro(3SH)) and 4-mercaptoproline (Pro(4SH)), Tpr(O), Met(O), Tpr(O$_2$) or Met(O$_2$), and the geometric isomers thereof, whilst any hydroxy and amino groups contained therein may be protected by conventional protecting groups (e.g. acyl, carbamoyl or aralkyl (especially benzyl), particularly those wherein $R^1$ denotes aryl, heteroaryl, aralkyl, heteroaralkyl, aryloxyalkyl, arylalkyloxy, di(arylalkyl)-aminoalkyl (wherein aryl denotes phenyl or mono- or di-substituted phenyl; the substituents of the phenyl group independently of one another are halogen or alkoxy; heteroaryl denotes indolyl, indolyl substituted by alkyl or benzyl in position 1 or pyridyl; and the alkyl- or alkoxy group contains 1 to 3 carbon atoms), particularly

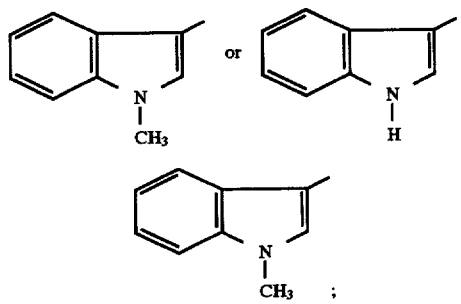

preferably wherein $R^1$ is
and/or wherein
A is an amino acid which has no or one polar functional group in the side chain, such as —OH, —COOH, —NH$_2$, guanidine, —CONH$_2$, —SH; particularly wherein the functional group in the side chain of A is OH, or
wherein A is Ser, Thr, Trp(For) or Tyr, or
wherein A is Pro or 4-hydroxyproline, preferably
wherein A is 4-hydroxyproline with a 2-S-configuration, particularly

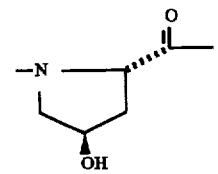

Of the compounds of formula I according to the invention, other preferred compounds are those wherein Y and Z independently of one another are methoxy or hydrogen or together denote —OCH$_2$O— or Y is hydrogen and Z is chlorine.

Of the compounds of formula I according to the invention, other preferred compounds are those wherein
m is 1 or 2,
G is chlorine, bromine or ethyl and
G is fluorine and m is 5.

The amino acids specified are preferably in the S-configuration.

Test results for compounds according to the invention:

The receptor affinity for the NK$_1$-receptor (substance P-receptor) was determined on human lymphoblastoma cells (IM-9) with cloned NK$_1$-receptors, by measuring the displacement of $^{125}$I-labelled substance p. The IC$_{50}$ values thus obtained are:

Compound of Example 1: 0.4 nM
Compound of Example 6: 0.75 nM

The compounds according to the invention are valuable neurokinin (tachykinin) antagonists which have, in particular, substance P-antagonism but also neurokinin A or neurokinin B-antagonistic properties. They are useful for treating and preventing neurokinin-mediated diseases such as respiratory diseases, e.g. asthma, bronchitis, rhinitis, cough or expectoration as well as inflammatory eye diseases such as conjunctivitis, inflammatory skin diseases such as dermatitis and urticaria, other inflammatory diseases such as polyarthritis or osteoarthritis, gastrointestinal diseases such as irritable colon and vomiting, as well as pain such as migraine.

The invention therefore also relates to the use of the compounds according to the invention as palliatives and pharmaceutical preparations which contain these compounds. They are preferred for use in humans. The compounds according to the invention may be administered by intravenous, subcutaneous, intramuscular, intraperitoneal, intranasal, inhalative or transdermal route, if desired with the aid of iontophoresis or enhancers known from the literature, and by oral route.

For parenteral administration, the compounds of formula I or the physiologically acceptable salts thereof, possibly with the conventional substances such as solubilisers, emulsifiers or other excipients, are put into solution, suspension or emulsion. Examples of solvents include: water, physiological saline solutions or alcohols, e.g. ethanol, propanediol or glycerol, sugar solutions such as glucose or mannitol solutions or a mixture of various solvents.

In addition, the compounds may be administered by implants, e.g. of polylactide, polyglycolide or polyhydroxybutyric acid, or by intranasal route.

The compounds according to the invention may be prepared by generally known methods of amino acid and peptide chemistry.

The components $R^1$—COOH, the amino acid H—A—OH and the amine H—$R^2$ are linked together. Either the carboxylic acid $R^1$—COOH can first be coupled with a suitably protected form of H—A—OH and then condensed with the amine H—$R^2$ after the protecting groups have been cleaved, or the suitably protected amino acid H—A—OH may first be reacted with H—$R^2$ and this product be coupled with $R^1$—COOH after deprotection.

The basic structures of the amines H—$R^2$ according to the invention may be obtained using methods known per se, e.g. according to A. L. Davis et al., J. Med. Chem. 18, 752 (1975) or H. Merz, DE 38 23 576 (C.A. 114 (21), 207 052 m). This preparation can be summarised by the reaction plan shown hereinafter. The benzyl group R' is inserted into a compound of general formula XI by reaction with NaH and BrR', ClR' or IR'. This reaction may be carried out with or without the use of a protecting group (Sch) on the exocyclic N.

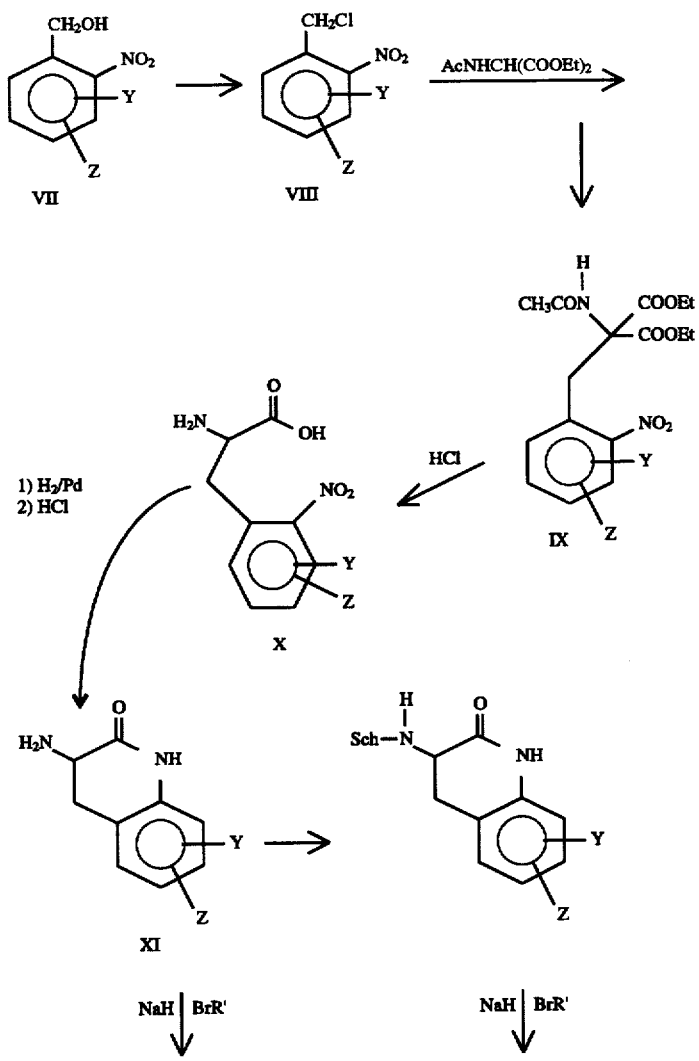

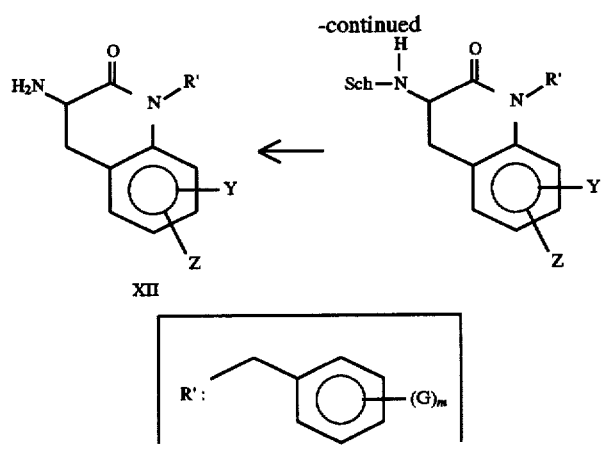

Suitable protecting groups (ScH) are base-stable protecting groups such as the Boc group.

In order to prepare a compound of general formula XI, a compound of general formula X is reduced and cyclised (e.g. analogously to the method described by A. L. Davis et al. (J. Med. Chem. 9, 826 (1966)) by means of Pd-black).

The compound X can be prepared from the correspondingly substituted 1-nitrobenzyl alcohol (VII) via the intermediates VIII and IX (by halogenation with, for example, $SOCl_2$ and subsequent reaction with diethylacetamidomalonate according to J. Med. Chem. 9, 828 (1966)).

In order to prepare a compound of general formula XII, it is also possible to use HalR' in general, especially ClR', instead of BrR'.

EXAMPLE 1 AND 2 (*R/S)

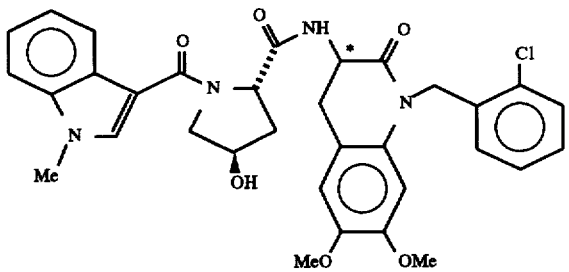

A. Preparation of the Starting Compound

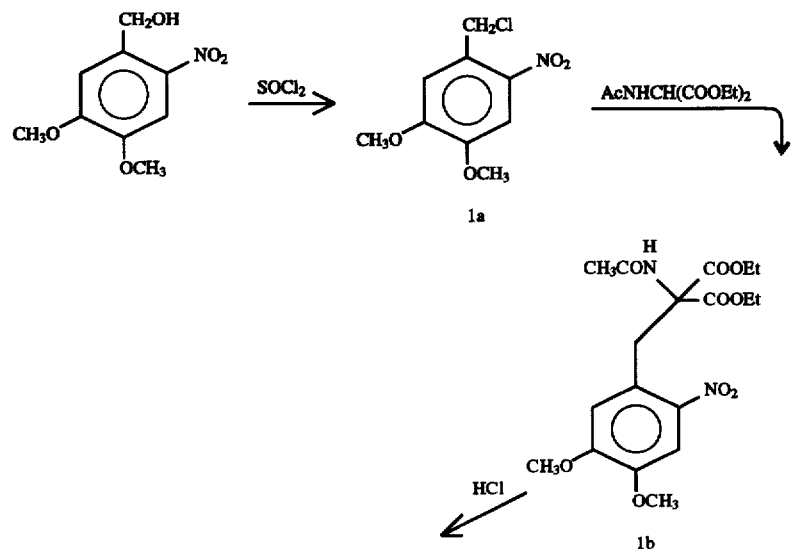

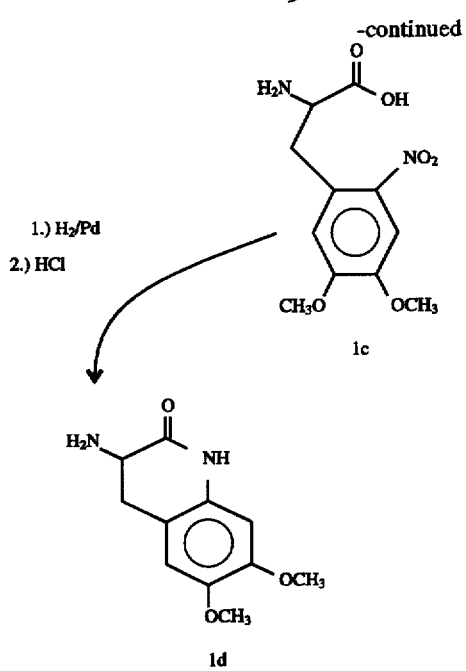

Preparation of 1a:

10.7 g of 6-Nitroveratryl alcohol are suspended in 20 ml of absolute $SOCl_2$ and 2.7 ml of absolute pyridine, heated to boiling and then a mixture of 4 ml of thionyl chloride and 2 ml of $CH_2Cl_2$ is added dropwise over half an hour. The mixture is then refluxed for a further hour, then cooled and the reaction mixture is stirred into a mixture of 20 g of ice and 20 g of water. The organic phase is washed thoroughly with water and $NaHCO_3$ solution, dried with $Na_2SO_4$ and evaporated down using a rotary evaporator. 11.4 g of 1a are obtained in the form of a dark brown oil (yield 98%).

Preparation of 1b:

11.2 g of 1a are reacted with 10.5 g of diethyl acetamido malonate as described in J. Med. Chem. 9, 828 (1966) to obtain 16.2 g of 1b in the form of yellow crystals (yield 81%). Mp.: 176°–178° C.

Preparation of 1c:

Using the method of A. L. Davis (J. Med. Chem. 9, 828, (1966)), 16 g of 1b were hydrolysed with 120 ml of concentrated hydrochloric acid, to obtain initially 1c.HCl. This is then converted with ammonia into the free amino acid 1c, of which 7.4 g are obtained in the form of greenish crystals (yield 71%). Mp.: about 207° C. (decomp.).

Preparation of 1d:

5.4 g of 1c were hydrogenated using 0.6 g of Pd-black as described by A.L. Davis et al. (J. Med. Chem. 9, 828 (1966)). The resulting amino compound was refluxed together with 68 ml of ethanol and 12 ml of concentrated hydrochloric acid for half an hour with stirring. After cooling, 26 ml of ether were added, the mixture was suction filtered and the precipitate was washed with ice-cold ethanol and ether and dried at 80° C. 3.3 g of 1d.HCl were obtained in the form of a light grey solid (yield 63%). Mp.: about 296° C. (decomp.).

B. 12.9 g of (±)-3-amino-6,7-dimethoy1,2,3,4-tetrahydroquinolin-2-one were dissolved in a mixture of 125 ml of dioxane and 125 ml of water, 12 g of $(Boc)_2$ were added and 2.9 g of sodium carbonate were stirred in. After one hours' stirring at ambient temperature the precipitate was suction filtered, washed with water and dried; in this way 12.3 g of (±)-3-Boc-amino-6,7-dimethoxy1,2,3,4-tetrahydroquinolin-2-one were obtained. Mp 155°–157° C.

1 g of the resulting substance was dissolved in 15 ml of DMF and 0.13 g of NaH dispersion (60% in oil) was added. After 0.5 hours a solution of 0.38 ml of 2-chlorobenzyl chloride dissolved in 5 ml of DMF was added and the resulting mixture was stirred for 5 hours at ambient temperature. Then 200 ml of ice-cold water were added and the resulting crystals were suction filtered, washed with water and dried. 1.28 g of (±)-3-Boc-amino-1-(2-chlorobenzyl)-6,7-dimethoxy1,2,3,4-tetrahydroquinolin-2-one were obtained.

In order to cleave the Boc group, 1.26 g of the above compound were combined with 32.5 ml of 4 n HCl in dioxane and 2.3 ml of anisole and stirred for 1.5 hours at ambient temperature. The reaction mixture was concentrated by evaporation under reduced pressure, the residue was stirred with 150 ml of ether and the resulting crystals were suction filtered, washed with ether and dried. 0.96 g of (±)-3-amino-1-(2-chlorobenzyl)-6,7-dimethoxy1,2,3,4-tetrahydroquinolin-2-one hydrochloride were obtained.

Coupling step:

0.96 g of the resulting compound were combined with 0.72 g of (2S,4R)-N-(1-methylindol-3-ylcarbonyl)-4-hydroxyproline, 40 ml of DMF, 0.8 ml of triethylamine (=TEA) and 0.84 g of benzotriazolyl-tetramethyl-uronium tetrafluoroborate (=TBTU), the pH was adjusted to 8.5 to 9 by the addition of TEA and the mixture was stirred for 1.5 hours at ambient temperature. The reaction mixture was stirred into 400 ml of saturated $NaHCO_3$ solution, the precipitate formed was suction filtered, washed with water, ethyl acetate and ether and dried. 0.92 g of the compound of Example 2 were obtained as an approximately 1:1 mixture of R/S-diastereomers. Mp.: 166°–168° C. $[\alpha]D^{20}$ (DMSO) =−74.0°.

Separation of diastereomers: 0.84 g of the mixture of diastereomers obtained was combined with 25 ml of $CH_2Cl_2$ and 25 ml of water, shaken several times and treated in an ultrasound bath and the suspension was left to stand for 4 days at ambient temperature. It was filtered, the $CH_2Cl_2$ phase was dried and concentrated by evaporation, to yield 0.16 g of the compound of Example 1 as a pure diastereomer. Mp.: 130°–132° C. [α]D²⁰ (DMSO)=+12.5°

List of Examples which can be prepared analogously:

TABLE 1

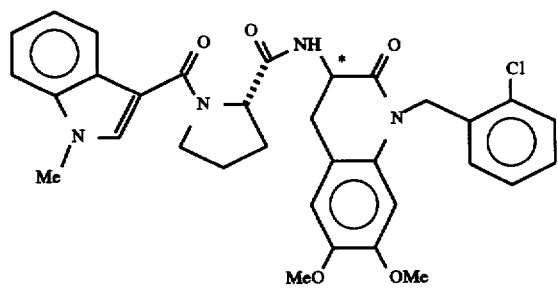

| Example No. | G¹ | G² | G³ | G⁴ | G⁵ | * |
|---|---|---|---|---|---|---|
| 1 | Cl | H | H | H | H | |
| 2 | Cl | H | H | H | H | R/S |
| 3 | Br | H | H | H | H | p.d. |
| 4 | Br | H | H | H | H | p.d. |
| 5 | F | H | H | H | H | R/S |
| 6 | CH₂CH₃ | H | H | H | H | p.d. |
| 7 | CH₂CH₃ | H | H | H | H | p.d. |
| 8 | Cl | Cl | H | Cl | H | |
| 9 | Cl | H | Cl | H | H | |
| 10 | F | F | F | F | F | | p.d.: pure diastereomer

EXAMPLE 11

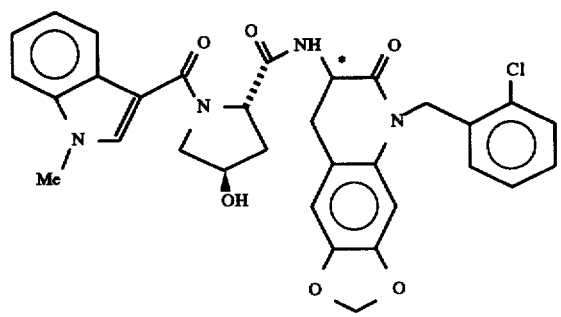

EXAMPLE 12

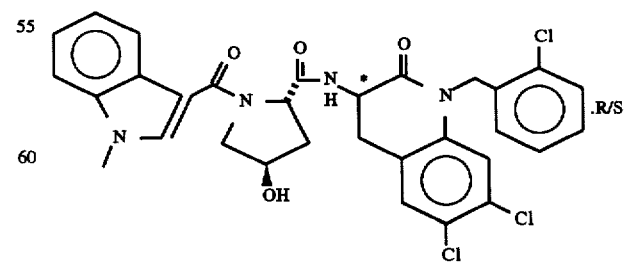

Physical data of the compounds:

EXAMPLE 3

Mp.: 100°–110° (decomp.); [α]D²⁰ (DMSO)=+13.8°

EXAMPLE 4

Mp.: 125°–140° (decomp.); [α]D²⁰ (DMSO)=−121.4°

EXAMPLE 5

Mp.: 141°–146° C.; [α]D²⁰ (MeOH)=−71.0°

EXAMPLE 6

Mp.: 128°–134° C. (decomp.); [α]D²⁰ (DMSO)=+0.6°

EXAMPLE 7

Mp.: 161°–168° C.; [α]D²⁰ (DMSO)=−130.4°

EXAMPLE 8

(G¹=G²=Cl; G³=G⁴=G⁵=H) was separated into the diastereomers.

EXAMPLE 8a

Mp: 212°–217° C.; [α]²⁰_D (DMSO)=−143.6°

EXAMPLE 8b

Mp: 148°–152° C.; [α]²⁰_D (DMSO)=+21.2°

EXAMPLE 10 (G¹–G⁵=F; R/S;

Mp.: 143°–153° C.; [α]²⁰_D (DMSO)=−77.2°

EXAMPLE 13 AND 14 (pure diastereomer)

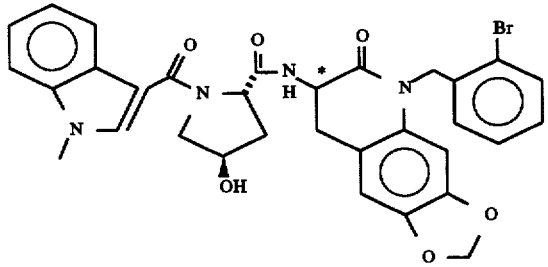

EXAMPLE 13

Mp: 186°–196° C.; [α]²⁰_D (DMSO)=−119.8°

EXAMPLE 14

Mp.: from 110° C. decomp.; [α]²⁰_D (DMSO)=+3.6°

EXAMPLE 15

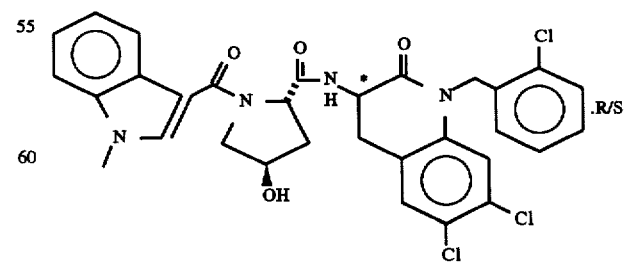

Mp: 244°–255° C.; [α]²⁰_D (DMSO)=−46.1°

EXAMPLE 16

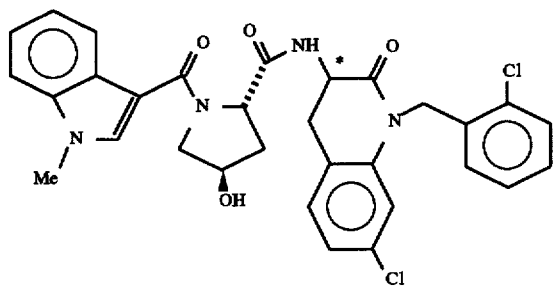

The starting compound used is (±)-3-amino-7-chloro-1,2,3,4-tetrahydroquinolin-2-one the preparation of which is described in the literature (T. J. McCord et al., J. Heterocycl. Chem. 9, 119 (1972); A. L. Davis et al., J. Med. Chem. 18, 752 (1975)).

11.1 g of this compound are dissolved in a mixture of 125 ml of dioxane and 125 ml of water, $(Boc)_2O$ is added and 2.9 g of sodium carbonate are added, with stirring. After one hours' stirring at ambient temperature the precipitate is suction filtered, washed with water and dried. In this way (±)-3-Boc-amino-7-chloro1,2,3,4-tetrahydroquinolin-2-one is obtained. 0.9 g of the compound obtained is dissolved in 15 ml of DMF and mixed with 0.13 g of NaH dispersion (60% in oil). After 0.5 hours a solution of 0.38 ml of 2-chlorobenzyl chloride dissolved in 5 ml of DMF is added and the mixture is stirred for 5 hours at ambient temperature. Then 200 ml of ice-cold water are added, the crystals obtained are suction filtered, washed with water and dried. In this way (±)-3-Boc-amino-1-(2-chlorobenzyl)-7-chloro1,2,3,4-tetrahydroquinolin-2-one is obtained.

1.2 g of the compound thus obtained is mixed with 32.5 ml of 4N HCl in dioxane and 2.3 ml of anisole and stirred for 1.5 hours at ambient temperature. The reaction mixture is evaporated down under reduced pressure, the residue is stirred with 150 ml of ether, the crystals obtained are suction filtered, washed with ether and dried. In this way (±)-3-amino-1-(2-chlorobenzyl)-7-chloro1,2,3,4-tetrahydroquinolin-2-one hydrochloride is obtained.

Coupling step:

0.88 g of the hydrochloride obtained is combined with 0.72 g of (2S, 4R)-N-(1-methylindol-3-yl-carbonyl)-4-hydroxyproline, 40 ml of DMF, 0.8 ml of TEA and 0.84 g of TBTU, the pH is adjusted to 8.5 to 9 by the addition of TEA and stirred for 1.5 hours at ambient temperature. The reaction mixture is stirred into 400 ml of saturated $NaHCO_3$ solution, the precipitate formed is suction filtered, washed with water, ethyl acetate and ether and dried. In this way the compound of Example 16 is obtained as an approximately 1:1 mixture of the R/S-diastereomers.

TABLE 2

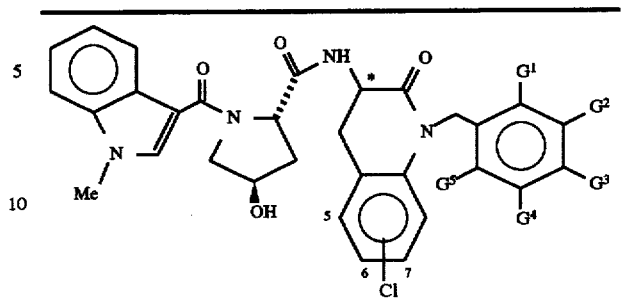

| Example No. | $G^1$ | $G^2$ | $G^3$ | $G^4$ | $G^5$ | Cl in position |
|---|---|---|---|---|---|---|
| 16 | Cl | H | H | H | H | 7 |
| 17 | Br | H | H | H | H | 7 |
| 18 | Cl | Cl | H | H | H | 7 |
| 19 | F | F | F | F | F | 7 |
| 20 | $CH_3$ | H | H | H | H | 7 |
| 21 | $CH_2CH_3$ | H | H | H | H | 7 |
| 22 | $OCH_3$ | H | H | H | H | 7 |
| 23 | Cl | H | H | H | H | 6 |
| 24 | Br | H | H | H | H | 6 |
| 25 | Cl | H | H | H | H | 5 |
| 26 | Br | H | H | H | H | 5 |
| 27 | Cl | H | H | H | H | 8 |

EXAMPLE 17

Mp.: 152°–162° C.; $[\alpha]D^{20}$ (MeOH)=–88.6°

EXAMPLE 23

Mp.: 158°–195° C.; $[\alpha]D^{20}$ (DMSO)=–48.2°

EXAMPLE 25

Mp.: 85°–100° C.; $[\alpha]D^{20}$ (DMSO)=–54.5°

EXAMPLE 27

Mp.: 78°–100° C.; $[\alpha]D^{20}$ (MeOH)=–85.2°

EXAMPLE 28

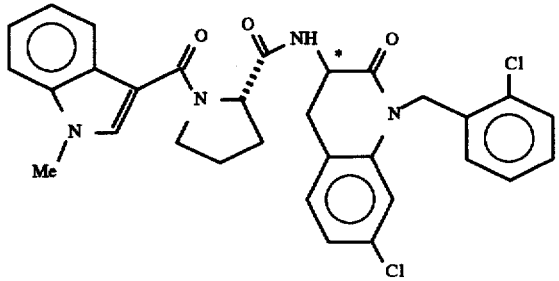

Pharmaceutical preparations:

Injectable solution 200 mg of active substance*
1.2 mg of monopotassium dihydrogen phosphate = $KH_2PO_4$
0.2 mg of disodium hydrogen phosphate = $NaH_2PO_4 \cdot 2H_2O$ (buffer)
94 mg of sodium chloride (isotonic)
or

-continued

| Pharmaceutical preparations: |
|---|
| 520 mg of glucose |
| 4 mg of albumin (protease protection) |
| q.s. sodium hydroxide solution |
| q.s. hydrochloric acid to adjust the pH to pH 6 |
| sufficient water to make a 10 ml solution for injections |
| Injectable solution |
| 200 mg of active substance* |
| 94 mg of sodium chloride |
| or |
| 520 mg of glucose |
| 4 mg of albumin |
| q.s. sodium hydroxide solution |
| q.s. hydrochloric acid to adjust the pH to pH 6 |
| sufficient water to make a 10 ml solution for injections |
| Freeze-dried preparation |
| 200 mg of active substance* |
| 520 mg of mannitol (isotonic substance/structural component) |
| 4 mg of albumin |
| Solvent 1 for freeze-dried material |
| 10 ml of water for injections |
| Solvent 2 for freeze-dried material |
| 20 mg Polysorbate ® 80 = Twen ® 80 (surfactant) |
| 10 ml of water for injections |

*Active substance: compounds according to the invention, e.g. the compounds of Example 1.
Dose for person weighing 67 kg: 1 to 500 mg

What is claimed is:

1. An amino acid derivative of formula (I)

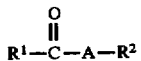

(I)

or a pharmaceutically acceptable salt thereof, wherein
R1 is

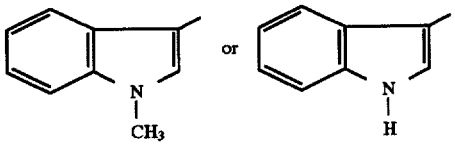

A is 3,4-didehydroproline (Δ(3,4)-Pro), 3-hydroxyproline (Pro(3 OH)), 3-aminoproline (Pro (3NH$_2$)), 4-aminoproline (Pro(4NH$_2$)), 5-hydroxypiperidine-2-carboxylic acid, or 4-mercaptoproline (Pro(4SH))
and $R^2$ is an amino of formula II

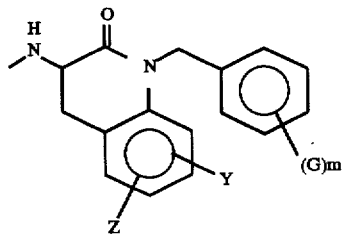

wherein
G is fluorine, chlorine, bromine, methyl, ethyl or methoxy
m is an integer 1,2,3,4 or 5
Y and Z, independent of one another, are hydrogen, (C$_{1-5}$) alkyl, (C$_{1-5}$)alkyloxy, benzyloxy, [wherein the phenyl group is unsubstituted or has 1, 2, or 3 substituents which, independently of each other, are (C$_{1-5}$)alkyl, (C$_{1-5}$)alkyloxy, dimethylamine, halogen, trifluoromethyl, —CN or —OCF$_3$], —OCF$_3$, halogen, —CF$_3$, —CN, —CH$_2$NH$_2$, —CONH$_2$,— N—(C$_{1-5}$-alkyl)$_2$, —NH—(C$_{1-4}$)-alkylcarbonyl, —N—(C$_{1-5}$)-alkyl-N-(C$_{1-4}$)-alkylcarbonyl, —NH$_2$ or a —NH—(C$_{1-5}$)-alkyl, or, if Y and Z are arranged vicinally to each other, they together represent —OCH$_2$O—, —OCH$_2$CH$_2$O— or —(CH$_2$)$_4$—.

2. The amino acid derivative as recited in claim 1 wherein in $R^2$, Y and Z, independent of one another, are methyl or methoxy.

* * * * *

UNITED STATES PATENT AND TRADEMARK OFFICE
CERTIFICATE OF CORRECTION

PATENT NO. : 5,712,397
DATED : January 27, 1998
INVENTOR(S) : F. Esser, et. al.

It is certified that error appears in the above-identified patent and that said Letters Patent is hereby corrected as shown below:

On the Title page, item [30], Foreign Application Prioriy Data should read --
Mar. 3, 1994    [DE]    Germany ......    44 06 884.0
Mar. 3, 1994    [DE]    Germany ......    44 06 885.8

Signed and Sealed this

Second Day of June, 1998

Attest:

BRUCE LEHMAN

Attesting Officer

Commissioner of Patents and Trademarks